United States Patent [19]

Schmolka

[11] 4,343,785

[45] Aug. 10, 1982

[54] GEL DENTIFRICE COMPOSITIONS

[75] Inventor: Irving R. Schmolka, Grosse Ile, Mich.

[73] Assignee: BASF Wyandotte Corporation, Wyandotte, Mich.

[21] Appl. No.: 291,263

[22] Filed: Aug. 10, 1981

[51] Int. Cl.$^3$ .......................... A61K 7/16; A61K 7/18; A61K 7/22
[52] U.S. Cl. ........................................ 424/49; 424/52; 424/54
[58] Field of Search ..................................... 424/49–58

[56] References Cited

U.S. PATENT DOCUMENTS

| | | | |
|---|---|---|---|
| 2,677,700 | 5/1954 | Jackson et al. | 424/49 |
| 2,773,801 | 12/1956 | Fox | 424/49 |
| 4,011,309 | 3/1977 | Lutz | 424/49 |
| 4,206,198 | 6/1980 | Schmolka | 424/49 |

OTHER PUBLICATIONS

Reng Parfuem Kosmet (1976) 57 (11): 307–316 "Foaming Agents for Products for Oral and Dental Hygeine".

*Primary Examiner*—Shep K. Rose
*Attorney, Agent, or Firm*—Joseph D. Michaels

[57] ABSTRACT

A gel dentifrice containing a cogeneric mixture of conjugated polyoxybutylene-polyoxyethylene block copolymers retards plaque formation and growth, and remains a gel below about 20° C.

10 Claims, No Drawings

GEL DENTIFRICE COMPOSITIONS

BACKGROUND OF THE INVENTION

1. Field of the Invention

The invention relates to a gel dentifrice comprising at least about 15 percent by weight of a polyoxybutylene-polyoxyethylene block copolymer, an effective amount of an essential additive and less than about 85 percent by weight of water. The gel dentifrice retards plaque formation and growth, and may be used to prepare a desensitizing dentrifice composition. The block copolymers provide stable gel products, at temperatures below about 30° C. and can be stored in the refrigerator or freezer without losing their gel characteristics.

2. Description of the Prior Art

U.S. Pat. No. 4,011,309 relates to a dentifrice composition and method for desensitizing teeth. The dentifrice composition is an aqueous gel comprising citric acid, sodium citrate, a block copolymer which is the condensation product of a normally solid, water-soluble high molecular weight condensation product of ethylene oxide and polypropylene glycol containing about 70 percent polyoxyethylene and water.

One of the problems of the prior art dentifrice gels is that the gel dentifrices liquify at temperatures below about 30° C. It has now been unexpectedly found that gel dentifrices prepared from the polyoxybutylene-polyoxyethylene block copolymers of the present invention provide stable gel products at temperatures of 20° C. and below.

SUMMARY OF THE INVENTION

The invention relates to a dentifrice comprising at least about 15 percent by weight of a polyoxybutylene-polyoxyethylene block copolymer, an effective amount of an essential additive and less than about 86 percent by weight of water relative to the total weight of block copolymer and water, said block copolymer being a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains. The average molecular weight of the polyoxybutylene polymers in the mixture is at least 1200, as determined by hydroxyl number and the oxyethylene groups present constitute about 50 to about 80 percent by weight of the compound, with the provisos that (a) when the hydrophobe molecular weight is about 1200, then the minimum polyoxyethylene content is about 60 percent by weight of the block copolymer and the minimum block copolymer content to form a gel is about 25 percent by weight of the aqueous gel composition;

(b) when the hydrophobe molecular weight is about 1800, then the minimum polyoxyethylene content is about 55 percent by weight of the block copolymer and the minium block copolymer content to form a gel is about 20 percent by weight of the aqueous gel composition;

(c) when the hydrophobe molecular weight is about 2400, then the minimum polyoxyethylene content is about 50 percent by weight of the block copolymer and the minimum block copolymer content to form a gel is about 16 percent by weight of the aqueous gel composition;

(d) when the hydrophobe molecular weight is about 3000, then the minimum polyoxyethylene content is about 45 percent by weight of the block copolymer and the minimum block copolymer content to form a gel is about 16 percent by weight of the aqueous gel composition.

DESCRIPTION OF THE PREFERRED EMBODIMENTS

The block copolymer of use in the invention is a cogeneric mixture of conjugated polyoxybutylene polyoxyethylene compounds having as a hydrophobe, a polyoxybutylene polymer of at least 1200 molecular weight. The polyoxybutylene compounds are prepared by first condensing butylene oxide with an organic compound containing a plurality of reactive hydrogen atoms to prepare a polyoxybutylene polymer of at least 1200 molecular weight, and subsequently condensing ethylene oxide thereto. The compounds used in this invention conform to the following generic formula:

$$Y[(C_4H_8O)_n\text{-E-H}]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 1200, as determined by hydroxyl number; E is a polyoxyalkylene chain wherein the oxygen/carbon atom ratio is at least 0.5, and E constitutes 50 percent by weight to 80 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 50 and 80 percent by weight of the resultant compound, with the polyoxybutylene polymer. These compounds have the following formula $$Y[(C_4H_8O)_n(C_2H_4O)_mH]_x \qquad (C)$$

wherein Y, n and x are defined as in Formula A and m has a value such that the oxyethylene groups constitute 50 to 80 percent by weight of the compound.

When ethylene oxide is condensed with a polyoxybutylene glycol of at least 1200 molecular weight and derived from a butane diol initiator, the resulting compounds have the following structure:

$$HO(C_2H_4O)_{m'}(C_4H_8O)_n(C_2H_4O)_mH \qquad (D)$$

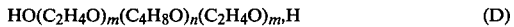

where n is defined as previously set forth; and m'+m have a value such that the oxyethylene groups constitute 50 percent by weight to 80 percent by weight, preferably 60 percent by weight to 70 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators, which may include water, diols such as propanediol, butanediol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine, an alkanolamine such as ethanolamine, may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, other 4-carbon cyclic ethers such as methyl oxetane, tetrahydrofuran and isobutylene oxide may be used.

The preferred block copolymers, conforming to structure D above of use in this invention, are those block copolymers which contain a minimum hydrophobe average molecular weight of 1200 and preferably 1600 or higher, including 2000, 3000 and preferably 1800 and 2400. The percent ethylene oxide in the block copolymer varies between about 50 percent by weight and about 80 percent by weight, preferably about 60 percent by weight to about 70 percent by weight of the block copolymer.

At least one of the essential additives, a cationic antidecay agent, a fluorine-containing compound or a desensitizing agent, is present in the gel dentifrice of this invention.

The cationic anti-decay agents which may be used as an essential additive in the invention may be any well known anti-bacterial agent such as the following: $N^1$-(4-chlorobenzyl)-$N^5$-(2,4-dichlorobenzyl) biguanide, p-chlorophenyl biguanide, 4-chlorobenzhydryl biguanide, 4-chlorobenzhydrylguanylurea, $N^3$-lauroxypropyl-$N^5$-p-chlorobenzylbiguanide, 1,6-di-(p-chlorophenyl-biguanido)hexane, 1-(lauryldimethylammonium)-8-(p-chlorobenzyldimethylammonium)octane dichloride, 5,6-dichloro-2-guanidinobenzimidazole, $N^1$-p-chlorophenyl-$N^5$-laurylbiguanide, 5-amino-1,3,bis(2-ethylhexyl)-5-methylhexahydropyramidine, clorhexidine gluconate, palmitic amido betaine and their non-toxic acid addition salts. The cationic anti-decay agent is used in an amount between 0.01 percent by weight and 5 percent by weight and preferably between 0.05 percent by weight and 1 percent by weight of the dentifrice.

The gel dentifrice may also contain as an essential additive a fluorine-containing compound having a beneficial effect on the care and hygiene of the oral cavity, such as sodium fluoride, or stannous fluoride, in an amount up to 1 percent, preferably between 0.1 percent by weight and 1 percent by weight of the dentifrice based on the water soluble fluorine content thereof.

The gel dentifrice may also contain as an essential additive a desensitizing agent such as a combination of citric acid and sodium citrate used in an amount of between 0.1 to 3, preferably from about 0.2 to about 1 percent citric acid and between about 0.3 and about 9, preferably 0.6 to about 3 percent by weight sodium citrate.

Useful optional additives, such as humectants or binders, which may be used in the gel dentifrices of the invention, are glycerin or sorbitol or both. Gelling agents such as methyl cellulose, carboxymethyl cellulose and gum tragacanth also may be used along with the polyoxybutylene-poloxyethylene gelling agents of this invention. A polishing agent such as colloidal silica for clear gels or calcium carbonate or calcium dihydrate for non-clear gels, may be used in an amount between 5 percent by weight and 50 percent by weight of the dentifrice. Other optional additives include color whitening agents, preservatives, solubilizing agents, silicones, chlorophyll compounds, urea and diammonium phosphate. Also useful are flavoring agents such as oils of spearmint, peppermint, wintergreen, sassafras, clove, sage, eucalyptus, marjoram, cinnamon, lemon, orange and sodium methylsalicylate, sweetening agents such as sucrose, lactose, maltose, sorbitol, sodium cyclamate, perillartin saccharin and sodium saccharin. Other optional additives as disclosed in U.S. Pat. Nos. 4,160,022, 4,117,107, 4,112,108 and Canada Pat. No. 1,039,656 may be used, with a maximum of 10 percent by weight of the gel dentifrice being placed on additives which tend to destroy the gel. These additives are used in an amount between 0.01 percent by weight and 5 percent by weight or more of the dentifrice.

As used herein, the term "gel" is defined as a solid or semisolid colloid containing considerable quantities of water. The particles in a gel are linked in a coherent meshwork with immobilizes the water. The colloidal solution with water as a dispersion medium is often called a "hydrosol". The gels within the scope of the present invention are more specifically "ringing" gels and may be described as gels that have a firm, jelly-like consistency; that is, by tapping the gel lightly it will vibrate and return to its original configuration.

Not all of the block copolymers of Formula D above may be employed in the present invention. Because of the nature of aqueous solutions of these block copolymers, three variables affect the formation of the gels. These variables are the weight percent concentration of block copolymers in the aqueous gel, the molecular weight of the hydrophobe $(C_4H_8O)_n$ and the weight percent of the hydrophile portion $(C_2H_4O)_m + (C_2H_4O)_m$, of the copolymer. These minima define a minimum weight percent concentration of the block copolymer with a specific molecular weight polyoxybutylene hydrophobe having a minimum weight percent of ethylene oxide condensed thereto that is necessary to form a gel. Thus at the minimum concentration with a specific molecular weight hydrophobe, a minimum weight percent of ethylene oxide is required before a specific block copolymer will form a gel in an aqueous solution.

Illustrative block copolymers of formula D above which may be employed in the preparation of the gel dentifrice composition of the present invention, made from a polyoxybutylene hydrophobe prepared from condensing 1,2-butylene oxide with a 1,4-butanediol initiator, are presented in Table I.

The minimum weight percent concentrations in aqueous gels with specific molecular weight hydrophobes are set out in Table II.

TABLE I

| Block Copolymer | Molecular Weight of Hydrophobe (Avg.) | Weight Percent of Hydrophile (Avg.) | Approximate Total Molecular Weight of Copolymer T | F |
|---|---|---|---|---|
| A | 1800 | 60 | 4500 | 4200 |
| B | 1800 | 70 | 6000 | 5700 |
| C | 1800 | 80 | 9000 | 8130 |
| D | 1200 | 70 | 4000 | 3765 |
| E | 1200 | 80 | 6000 | 5160 |
| F | 2400 | 60 | 6000 | 5670 |
| G | 2400 | 70 | 8000 | 7800 |
| H | 2400 | 80 | 12,000 | 11,000 |
| I | 3000 | 60 | 7500 | 6165 |
| J | 3000 | 70 | 10,000 | 9000 |
| K | 3000 | 80 | 15,000 | 11,000 |
| L | 1200 | 60 | 3000 | 2922 |

TABLE II

| Molecular Weight of Hydrophobe | Minimum Percent by Weight of Block Copolymer to form Aqueous Gel | Minimum Percent by Weight of Ethylene Oxide Required |
|---|---|---|
| 1200 | 25 | 60 |
| 1600 | 20 | 55 |
| 2400 | 16 | 50 |
| 3000 | 16 | 45 |

The gels of the present invention comprise, based on a total of 100 parts by weight, (a) at least about 15 parts, preferably from about 15 parts to about 30 parts, more preferably from about 20 parts to about 25 parts, of polyoxybutylene-polyoxyethylene block copolymer; (b) less than about 85 parts, preferably from about 40 parts to about 80 parts, more preferably from about 50 parts to about 70 parts, of water; (c) optionally from about 4 parts to about 20 parts of optional additives, and (d) an effective amount of essential additives.

The technical explanation for the formation of the gels of the invention is not entirely understood, and the explanation hereinafter is not to be considered as being limitative of the invention. However, the behavior of these block copolymers in forming the gels is believed to be explained on the basis of hydrate formation. It may be speculated that the hydrophobe may, in its own right, immobilize the water independently of the oxyethylene chain by hydrogen bonding. It should be noted that the preferred block copolymers used in the gels of this invention exhibit a hydrophobe lying between two equal hydrophiles. This structure suggests a loose micellar structure is obtained with this class of nonionics and that gel formation would readily involve entrapment of free water in addition to water due to hydrogen bonding.

The gel dentifrice compositions of the invention are prepared by the following procedures.

1. (a) Heat water to 45°–50° C.; (b) add block copolymer at stated temperature with gentle stirring until the polymer is completely dissolved to get a homogeneous solution; (c) add additives and allow to cool to room temperature.

2. (a) Heat water to about 50° C.; (b) add block copolymer and maintain temperature 45°–50° C. with gentle stirring until the copolymer is completely dissolved and a homogeneous solution is obtained; (c) add desensitising additives stirring gently; (d) quickly transfer to tubes in which the dentifrice quickly sets up into a gel at about 35° C.

The following examples will further illustrate the various aspects of the invention. Where not otherwise specified throughout this specification and claims, temperatures are in degrees centigrade, and parts, percentages and proportions are by weight.

EXAMPLE 1

A gel dentifrice was prepared by placing 75 parts of water in a container and heating to 50° C. 25 parts of the polyoxybutylene-polyoxyethylene block copolymer, designated Black Copolymer A, are added and the mixture maintained at 45°–50° C., with gentle stirring until Block Copolymer A had completely dissolved and the system was homogeneous and fluid. To 90 parts by weight of the above solution were added 4 parts by weight glycerine, 0.3 parts by weight saccharine, 0.7 parts by weight spearmint and 5 parts by weight palmitic amido betaine (Schercotaine PAB, Scher Bros., NYC) to obtain the gel dentifrice.

EXAMPLE 2

To 92 parts by weight of the solution of block copolymer F and water prepared by the method of Example 1 were added 7 parts by weight glycerine, 1.5 parts by weight sodium citrate, 1 part by weight peppermint oil and 0.5 parts by weight citric acid and stirred gently for a few minutes until a clear homogeneous formulation had formed. The mixture was quickly transferred to tubes in which it quickly set up into a gel at 35° C.

The gels of this invention remain stable products at temperatures below about 20° C.

The embodiments of this invention in which an exclusive privilege or property is claimed are defined as follows:

1. A gel dentifrice comprising at least about 15 percent by weight of a polyoxybutylene-polyoxyethylene block copolymer, an effective amount of an essential additive and less than about 85 percent by weight of water, said block copolymer being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 1200, as determined by hydroxyl number, and the oxyethylene groups present constituting 50 to 80 percent by weight of the mixture, with the provisos that:

(a) when the hydrophobe molecular weight is about 1200, when the minimum polyoxyethylene content is about 60 percent by weight of the block copolymer and the minimum block copolymer content to form a gel is about 25 percent by weight of the aqueous gel compositions;

(b) when the hydrophobe molecular weight is about 1800, when the minimum polyoxyethylene content is about 55 percent by weight of the block copolymer and the minimum block copolymer content to form a gel is about 20 percent by weight of the aqueous gel composition;

(c) when the hydrophobe molecular weight is about 2400, then the minimum polyoxyethylene content is about 50 percent by weight of the block copolymer and the minimum block copolymer content to form a gel is about 16 percent by weight of the aqueous gel composition;

(d) when the hydrophobe molecular weight is about 3000, then the minimum polyoxyethylene content is about 45 percent by weight of the block copolymer and the minimum block copolymer content to form a gel is about 16 percent by weight of the aqueous gel composition.

2. The gel dentifrice of claim 1 wherein the block copolymer has an average molecular weight of the polyoxybutylene polymer of about 1800.

3. The gel dentifrice of claim 1 wherein the block copolymer has an average molecular weight of the polyoxybutylene polymer of about 1800 and the oxyethylene groups constitute about 60 percent by weight of the mixture.

4. The gel dentifrice of claim 1 wherein the block copolymer has an average molecular weight of the polyoxybutylene polymer of about 1800 and the oxyethylene groups constitute about 70 percent by weight of the mixture.

5. The gel dentifrice of claim 1 additionally comprising an amount of optional additives between 4 percent by weight and 20 percent by weight of the gel dentifrice.

6. The gel dentifrice of claim 3 additionally comprising an amount of optional additives between 4 percent by weight and 20 percent by weight of the gel dentifrice.

7. The gel dentifrice of claim 6 wherein the optional additives are about 4 percent by weight glycerine, about 0.3 percent by weight sodium saccharine, about 0.7 percent by weight peppermint oil and the essential additive is about 5 percent by weight palmitic amido betaine.

8. The gel dentifrice of claim 6 wherein the additives are about 7 percent by weight glycerine, about 1 percent by weight peppermint oil, about 0.5 percent by weight citric acid and about 1.5 percent by weight sodium citrate.

9. The gel dentifrice of claim 1 wherein the polyoxybutylene-polyoxyethylene block copolymer is from about 15 to about 30 percent by weight, and the water is from about 40 to about 80 percent by weight.

10. The gel dentifrice of claim 9 additionally comprising an amount of optional additives between 4 percent by weight and 20 percent by weight of the gel dentifrice.

* * * * *